United States Patent [19]

Axen

[11] 4,207,420

[45] Jun. 10, 1980

[54] 2,2-DIFLUORO-PGF₁ ANALOGS

[75] Inventor: Udo F. Axen, Plainwell, Mich.

[73] Assignee: The Upjohn Company, Kalamazoo, Mich.

[21] Appl. No.: 724,160

[22] Filed: Sep. 17, 1976

Related U.S. Application Data

[62] Division of Ser. No. 552,708, Feb. 24, 1975, Pat. No. 4,001,300.

[51] Int. Cl.² ............................................. C07C 177/00
[52] U.S. Cl. ................................. 560/121; 562/503; 260/408
[58] Field of Search .............. 260/468 D, 514 D, 408; 560/121; 562/503

[56] References Cited

U.S. PATENT DOCUMENTS

| | | | |
|---|---|---|---|
| 3,767,695 | 10/1973 | Pike et al. ............................. | 260/468 |
| 3,816,393 | 6/1974 | Hayashi et al. ...................... | 260/468 |
| 3,847,967 | 11/1974 | Lincoln et al. ....................... | 260/468 |
| 3,855,270 | 12/1974 | Pike et al. ............................ | 260/468 |
| 3,929,861 | 12/1975 | Pike et al. ............................ | 260/468 |
| 3,962,293 | 6/1976 | Magerlein et al. .................... | 260/468 |

OTHER PUBLICATIONS

Burger, Medicinal Chemistry, pp. 81, 82 (1960).

*Primary Examiner*—Robert Gerstl
*Attorney, Agent, or Firm*—Robert A. Armitage

[57] ABSTRACT

2,2-Difluoro prostanglandin E, $F_\alpha$, $F_\beta$, A, and B analogs are disclosed with intermediates and with processes for making them. These compounds differ from the prostaglandins in that they have two fluoro atoms at the C-2 position in place of the two hydrogen atoms at C-2 in the prostaglandins. These compounds are useful for a variety of pharmacological purposes, including anti-ulcer, inhibition of platelet aggregation, increase in nasal patency, labor induction at term, and wound healing.

6 Claims, No Drawings

2,2-DIFLUORO-PGF₁ ANALOGS

The present application is a divisional application of Ser. No. 552,708, filed Feb. 24, 1975, now issued as U.S. Pat. No. 4,001,300, on Jan. 4, 1977.

The present invention relates to prostaglandin analogs for which the essential material constituting a disclosure therefor is incorporated by reference here from U.S. Pat. No. 4,001,300, issued Jan. 4, 1977.

I claim:

1. A compound of the formula

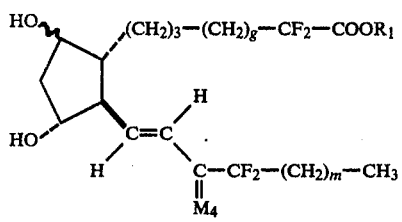

or a mixture comprising that compound and the entiomer thereof, wherein g is 2 to 4, inclusive;

wherein $M_4$ is

wherein m is 2 to 4, inclusive, wherein $R_1$ is hydrogen, alkyl or one to 12 carbon atoms, inclusive, cycloakyl of 3 to 10 carbon atoms, inclusive, aralkyl of 7 to 12 carbon atoms, inclusive, phenyl, phenyl substituted with one, 2, or 3 chloro, alkyl of one to 4 carbon atoms, inclusive, or a pharmacologically acceptable cation,

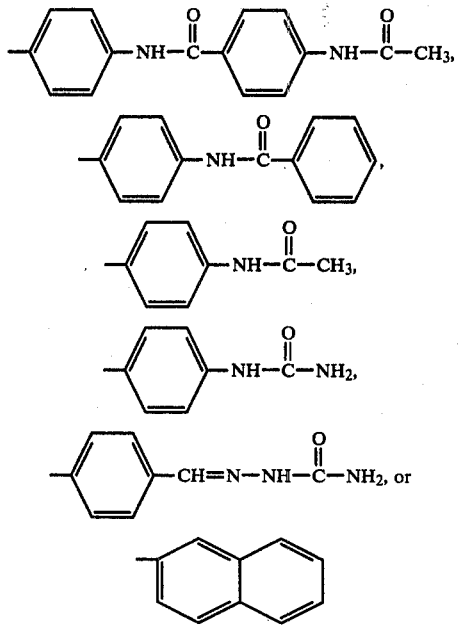

2. A compound according to claim 1, wherein $M_4$ is

3. A compound according to claim 2, wherein g is 2.
4. A compound according to claim 3, wherein m is 3.
5. 2,2,16,16-Tetrafluoro-PGF₁α, a compound according to claim 4, wherein $R_1$ is hydrogen.
6. 2,2,16,16-Tetrafluoro-PGF₁α, methyl ester, a compound according to claim 4, wherein $R_1$ is methyl.

* * * * *

UNITED STATES PATENT OFFICE
CERTIFICATE OF CORRECTION

Patent No. 4,207,420  Dated 10 June 1980

Inventor(s) Udo F. Axen

It is certified that error appears in the above-identified patent and that said Letters Patent are hereby corrected as shown below:

Column 1, lines 28-32, " 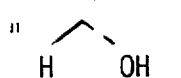 " should read -- 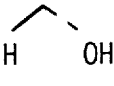 or 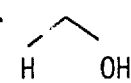 --.

Signed and Sealed this

Twenty-fourth Day of March 1981

[SEAL]

Attest:

RENE D. TEGTMEYER

Attesting Officer  Acting Commissioner of Patents and Trademarks